US 12,121,593 B2

(12) United States Patent
Saleem-Uddin et al.

(10) Patent No.: US 12,121,593 B2
(45) Date of Patent: Oct. 22, 2024

(54) THERAPY

(71) Applicant: The University of Bristol, Bristol (GB)

(72) Inventors: Moin Ahson Saleem-Uddin, Bristol (GB); Gavin Iain Welsh, Bristol (GB); Wen Yi Ding, Swindon (GB)

(73) Assignee: The University of Bristol, Bristol (GB)

( * ) Notice: Subject to any disclaimer, the term of this patent is extended or adjusted under 35 U.S.C. 154(b) by 92 days.

(21) Appl. No.: 17/348,048

(22) Filed: Jun. 15, 2021

(65) Prior Publication Data

US 2021/0402008 A1    Dec. 30, 2021

(30) Foreign Application Priority Data

Jun. 15, 2020  (GB) .................................. 2009039

(51) Int. Cl.
A61K 48/00     (2006.01)
C12N 15/86     (2006.01)

(52) U.S. Cl.
CPC ............ A61K 48/005 (2013.01); C12N 15/86 (2013.01); *C12N 2750/14143* (2013.01); *C12N 2830/48* (2013.01); *C12N 2830/50* (2013.01)

(58) Field of Classification Search
CPC .................. A61K 48/005; C12N 15/86; C12N 2750/14143; C12N 2830/48; C12N 2830/50; A61P 13/12
See application file for complete search history.

(56) References Cited

U.S. PATENT DOCUMENTS

| | | | |
|---|---|---|---|
| 5,122,458 A * | 6/1992 | Post | C12N 15/70 435/320.1 |
| 2003/0152954 A1 | 8/2003 | Antignac et al. | |
| 2018/0353619 A1 | 12/2018 | Michalakis et al. | |
| 2022/0125950 A1 | 4/2022 | Saleem-Uddin et al. | |

FOREIGN PATENT DOCUMENTS

| | | |
|---|---|---|
| CN | 105745326 A | 7/2016 |
| CN | 108368164 A | 8/2018 |
| EP | 4273243 A1 | 11/2023 |
| WO | WO-2001/53347 A2 | 7/2001 |
| WO | WO-2003082305 A1 | 10/2003 |
| WO | WO-2007/125723 A1 | 11/2007 |
| WO | WO-2015060722 A1 | 4/2015 |
| WO | WO-2017075619 A1 | 5/2017 |
| WO | WO-2017078100 A1 | 5/2017 |
| WO | WO-2017/144080 A1 | 8/2017 |
| WO | WO-2018/033254 A2 | 2/2018 |
| WO | WO-2018/144709 A2 | 8/2018 |
| WO | WO-2020/148548 A1 | 7/2020 |

OTHER PUBLICATIONS

Rheault MN, Gbadegesin RA. The Genetics of Nephrotic Syndrome. J Pediatr Genet. Mar. 2016;5(1):15-24. (Year: 2016).*

(Continued)

*Primary Examiner* — Jeremy C Flinders
*Assistant Examiner* — Thomas R. Amick
(74) *Attorney, Agent, or Firm* — MARSHALL, GERSTEIN & BORUN LLP

(57) ABSTRACT

The application provides gene therapies for treating monogenic forms of nephrotic syndrome.

16 Claims, 6 Drawing Sheets

Specification includes a Sequence Listing.

Cacctgaggtcaggagttcgagaccagcgtggccaacatgatgaaacccgtctctagtaaaaatacaaaaat
tagccaggcatggtgctatatacctgtagcaccagctacttgggagacagaggtgggagaattacttgaacctg
ggaggttcaagccatgggaggtggaagttgcagtgagccgagatgccactgcactccagcctgagcaacaga
gcaagactatctcaagaaaagaaagaaagaaagaaagagacttgccaaggtcatgtatcagggcaaggaag
agctgggggcccagctggctgctcccctgctgagctgggagaccaccttgatctgacttctcccatcttcccagc
ctaagccaggccctggggtcacggaggctggggaggcaccgaggaacgcgcctggcatgtgctgacagggg
attttatgctccagctgggccagctgggaggagcctgctgggcagaggccagagctgggggctctggaaggta
cctgggggaggttgcactgtgagaatgagctcaagctgggtcagagagcagggctgactctgccagtgcctgc
atcagcctcatcgctctcctaggctcctggcctgctggactctgggctgcaggtccttcttgaaaggctgtgagta
gtgagacaaggagcaggagtgaggggtggcaggagagaagatagagattgagagagagagagagagagag
acagagagagagggaagagacagagacaaaaggagagagaacggcttagacaaggagagaaagatggaaa
gataaagagactgggcgcagtggctcacgcctgtaatcccaacacttggggaggccaaggtgggaggatggc
ttgaaggaaagagtctgagatcaacctggccaacatagtgagaccccgtctctaaaaaaaaaagaaaaaaaa
aagaaaaaagaaaaaaaagttttttttaaagagacagagaaagagactcagagattgagactgagagcaaga
cagagagagatactcacagggaagaggggaagaggaaaacgagaaagggaggagagtaacggaaagaga
taaaaaagaaaagcaggtggcagagacacacagagagggacccagagaaagccagacagacgcaggtgg
ctggcagcgggcgctgtgggggtcacagtagggggacctgtg

SEQ ID NO: 1

(56) References Cited

OTHER PUBLICATIONS

Ikeda, Yoichiro1; Sun, Zhao1; Ru, Xiao2; Vandenberghe, Luk H.2,3,4; Humphreys, Benjamin D.1. Efficient Gene Transfer to Kidney Mesenchymal Cells Using a Synthetic Adeno-Associated Viral Vector. Journal of the American Society of Nephrology 29(9):p. 2287-2297, Sep. 2018 (Year: 2018).*
Makrides SC. Vectors for gene expression in mammalian cells. New Comprehensive Biochemistry. 2003;38:9-26. (Year: 2003).*
Choi JH, Yu NK, Baek GC, Bakes J, Seo D, Nam HJ, Baek SH, Lim CS, Lee YS, Kaang BK. Optimization of AAV expression cassettes to improve packaging capacity and transgene expression in neurons. Mol Brain. Mar. 11, 2014;7:17 (Year: 2014).*
Dany P. Perocheau et al, Age-Related Seroprevalence of Antibodies Against AAV-LK03 in a UK Population Cohort. Human Gene Therapy.Jan. 2019.79-87. (Year: 2019).*
Takeda et al. Nephron Experimental Nephrology (2004) 96 (4): e119-e126. (Year: 2004).*
Kestilä et al., "Positionally cloned gene for a novel glomerular protein-nephrin-is mutated in congenital nephrotic syndrome," Mol Cell, 1:575-582 (1998).
Luo et al., "Hepatorenal correction in murine glycogen storage disease type I with a double-stranded adeno-associated virus vector," Mol Ther, 19:1961-70 (2011).
Moeller et al., "Two gene fragments that direct podocyte-specific expression in transgenic mice," J Am Soc Nephrol, 13:1561-7 (2002).
Picconi et al. ,"Kidney-specific expression of GFP by in-utero delivery of pseudotyped adeno-associated virus 9," Molecular Therapy Methods & Clinical Development, 1:14014, 11 pages (2014).
Rocca et al., "rAAV9 combined with renal vein injection is optimal for kidney-targeted gene delivery: conclusion of a comparative study," Gene therapy, 21:618-628 (2014).
Schambach et al., "Woodchuck hepatitis virus post-transcriptional regulatory element deleted from X protein and promoter sequences enhances retroviral vector titer and expression," Gene Therapy, 13:641-645 (2005).
Schievenbusch et al., "Combined Paracrine and Endocrine AAV9 mediated Expression of Hepatocyte Growth Factor for the Treatment of Renal Fibrosis," Molecular Therapy, 18:1302-1309 (2010).
Van Der Wouden et al., Approaches and methods in gene therapy for kidney disease. J Pharmacol Toxicol Methods, 50:13-24 (2004).
Ding et al., "Adeno-Associated Virus Vector Gene Therapy Ameliorates Nephrosis in a Podocin-deficient Mouse Model of Nephrotic Syndrome", UK Kidney Week Virtual, Abstract (2019).
Ding, "Investigating adeno-associated virus as a vector for gene therapy for steroid-resistant nephrotic syndrome," British Library EThOS, Abstract (2019).
Needleman et al., "A General Method Applicable to the Search for Similarities in the Amino Acid Sequence of Two Proteins," Journal of Molecular Biology, 48(3):443-453 (1970).
Kawai et al., "Transient Expression of WHIM-Type Mutant CXCR4 Human Hematopeitic Stem Cells Mediated by Integration Defective Lentivirus Vector Enhance Engraftment in the NOD/SCID Mouse Xenograft Model," Molecular Therapy, 15, Supplement 1, p. S121-S122 (2007).
Bierzynska et al., "Genomic and clinical profiling of a national nephrotic syndrome cohort advocates a precision medicine approach to disease management", Kidney International., 91(4):937-947 (2017).
Caridi et al., "NPHS2 (Podocin) Mutations in Nephrotic Syndrome. Clinical Spectrum and Fine Mechanisms", Pediatric Research, 57(5, part 2), pp. 54R-61R (2005).
Dong et al., "Towards an understanding of kidney disease associated with WT1 mutations," Kidney International, 88:684-690 (2015).
Kemper et al., "Treatment of Genetic Forms of Nephrotic Syndrome", Frontiers in Pediatrics, 6(72), 8 pages (2018).
Tabatabaeifar et al., "An inducible mouse model of podocin-mutation-related nephrotic syndrome", PLOS One, 12(10), 21 pages (2017).
Zhang et al., "Research progress of monogenic mutations in the pathogenesis of steroid-resistant nephrotic syndrome", Journal of Rare Disease Research, 2024, vol. 3 issue 1, pp. 18-29.

\* cited by examiner

Fig. 1

Cacctgaggtcaggagttcgagaccagcgtggccaacatgatgaaaccccgtctctagtaaaaatacaaaaat
tagccaggcatggtgctatatacctgtagcaccagctacttgggagacagaggtgggagaattacttgaacctg
ggaggttcaagccatgggaggtggaagttgcagtgagccgagatgccactgcactccagcctgagcaacaga
gcaagactatctcaagaaaagaaagaaagaaagaaagagacttgccaaggtcatgtatcagggcaaggaag
agctgggggcccagctggctgctcccctgctgagctgggagaccaccttgatctgacttctcccatcttcccagc
ctaagccaggccctggggtcacggaggctggggaggcaccgaggaacgcgcctggcatgtgctgacagggg
attttatgctccagctgggccagctgggaggagcctgctgggcagaggccagagctgggggctctggaaggta
cctgggggaggttgcactgtgagaatgagctcaagctgggtcagagagcagggctgactctgccagtgcctgc
atcagcctcatcgctctcctaggctcctggcctgctggactctgggctgcaggtccttcttgaaaggctgtgagta
gtgagacaaggagcaggagtgaggggtggcaggagagaagatagagattgagagagagagagagagag
acagagagagaggaagagacagagacaaaaggagagagaacggcttagacaaggagagaaagatggaaa
gataaagagactgggcgcagtggctcacgcctgtaatcccaacacttggggaggccaaggtgggaggatggc
ttgaaggaaagagtctgagatcaacctggccaacatagtgagaccccgtctctaaaaaaaaaagaaaaaaaa
aagaaaaagaaaaaaaagttttttttaaagagacagagaaagagactcagagattgagactgagagcaaga
cagagagagatactcacagggaagaggggaagaggaaaacgagaaagggaggagagtaacggaaagaga
taaaaaagaaaagcaggtggcagagacacacagagagggacccagagaaagccagacagacgcaggtgg
ctggcagcgggcgctgtgggggtcacagtaggggggacctgtg

SEQ ID NO: 1

Fig. 2

Aatcaacctctggattacaaaatttgtgaaagattgactggtattcttaactatgttgctccttttac
gctatgtggatacgctgctttaatgcctttgtatcatgctattgcttcccgtatggcttttcattttctcc
tccttgtataaatcctggttgctgtctctttatgaggagttgtggcccgttgtcaggcaacgtggcgt
ggtgtgcactgtgtttgctgacgcaaccccactggttggggcattgccaccacctgtcagctcctt
tccgggactttcgctttccccctccctattgccacggcggaactcatcgccgcctgccttgcccgct
gctggacaggggctcggctgttgggcactgacaattccgtggtgttgtcggggaaatcatcgtcct
ttccttggctgctcgcctgtgttgccacctggattctgcgcgggacgtccttctgctacgtcccttcg
gccctcaatccagcggaccttccttcccgcggcctgctgccggctctgcggcctcttccgcgtcttc
gccttcgccctcagacgagtcggatctcccttttgggccgcctcccgc

SEQ ID NO: 2

Fig. 3 ctgtgccttctagttgccagccatctgttgtttgccccctccccgtgccttccttgaccctggaaggt
gccactcccactgtcctttcctaataaaatgaggaaattgcatcgcattgtctgagtaggtgtcatt
ctattctgggggtggggtggggcaggacagcaaggggaggattgggaagacaatagcagg
catgctggggatgcggtgggctctatgg

SEQ ID NO: 3

Fig. 4A aggggaagag gaaaacgaga aagggaggag agtaacggaa agagataaaa aagaaaagca
ggtggcagag acacacagag agggacccag agaaagccag acagacgcag gtggctggca
gcgggcgctg tgggggtcac agtaggggga cctgtgatgg ccctggggac gacgctcagg
gcttctctcc tgctcctggg gctgctgact gaaggcctgg cgcagttggc gattcctgcc tccgttcccc
ggggcttctg ggccctgcct gaaaacctga cggtggtgga gggggcctca gtggagctgc
gttgtggggt cagcacccct ggcagtgcgg tgcaatgggc caaagatggg ctgctcctgg
gccccgaccc caggatccca ggcttcccga ggtaccgcct ggaaggggac cctgctagag
gtgaattcca cctgcacatc gaggcctgtg acctcagcga tgacgcggag tatgagtgcc
aggtcggccg ctctgagatg gggcccgagc tcgtgtctcc cagagtgatc ctctccatcc tggttcctcc
caagctgctc tgctgaccc cagaggcagg caccatggtc acctgggtag ctgggcagga
gtacgtggtc aactgtgtgt ctggggacgc gaagccagca cctgacatca ccattctcct
gagtggacag acaatatctg acatctctgc aaacgtgaac gagggctccc agcagaaact
cttcactgtg gaggccacag ccagggtgac accccggagc tcagataata ggcagttgct
ggtctgtgag gcgtctagcc cagcactgga ggcccccatc aaggcctcat tcaccgtgaa tgttctgttc
cctccaggac cccctgtcat cgagtggcca ggcctggatg aggggcacgt gcgggcagga
cagagcttgg agctgccgtg cgtggcccga gggggtaatc ccttagccac actgcagtgg
ctgaagaatg gccagccggt gtccacagcg tggggcacag agcacaccca ggcggtggcc
cgcagtgtgc tggtgatgac cgtgaggcca gaagaccatg gagcgcagct cagctgcgag
gcccacaaca gcgtgtctgc agggacccag gagcacggca tcacactgca ggtcaccttt
cccccctagtg ccattattat cttgggatct gcatcccaga ctgagaacaa gaacgtgaca ctctcctgtg
tcagcaagtc cagtcgcccg cgggttctgc tacgatggtg gctgggctgg cggcagctgc
tgcccatgga ggagacagtc atggatggac tgcatggcgg tcacatctcc atgtccaacc
tgacattcct ggcgcggcgg gaggacaacg gtctgaccct cacatgtgag gccttcagtg
aagccttcac caaggagacc ttcaagaagt cgctcatcct gaacgtaaaa tatcccgccc
agaaactgtg gattgagggt cccccagagg ccagaagct ccgggctggg acccgggtga
ggctggtgtg tttggctatc gggggcaacc cagagccctc cctcatgtgg tacaaggact
cgcgcaccgt gaccgagtcg cggctgccgc aggagtcgcg gcgcgtgcat ctcggcagcg
tggagaaatc tgggagcacc ttctcccgag agctggtgct ggtcacaggg ccgtcggaca
accaggccaa gttcacgtgc aaggctggac agctcagcgc gtccacgcag ctggcggtgc
agtttcccc aactaacgtg acgatcctgg ccaacgcatc cgcactgcgc ccgggagacg
ccttaaactt gacatgcgtc agcgtcagca gcaatccgcc ggtcaacttg tcctgggaca
aggaagggga gaggctggag ggcgtggccg ccccaccccg gagagcccca ttcaaaggct
ccgccgccgc caggagcgtc cttctgcaag tgtcatcccg cgatcatggc cagcgcgtga
cctgccgcgc ccacagcgcc gagctccgcg aaaccgtgag ctccttctat cgcctcaacg
tactgtaccg tccagagttc ctgggggagc aggtgctggt ggtgaccgcg gtggagcagg
gcgaggcgtt gctgcccgtg tccgtgtccg ctaaccccgc ccccgaggcc ttcaactgga
ccttccgcgg ctatcgcctc agtccagcgg gcggccccccg gcatcgcatc ctgtccagcg
gggctctgca tctgtggaat gtgacccgcg cggacgacgg cctctatcag ctgcactgcc
agaactctga gggcaccgcg gaagcgcggc tgcggctgga cgtgcactat gctcccacca
tccgtgccct ccaggacccc actgaggtga cgtcgggggg ttctgtggac atagtctgca
ctgtcgatgc caatcccatc ctcccgggca tgttcaactg ggagagactg ggagaagatg
aggaggacca gagcctggat gacatggaga agatatccag

Fig. 4A cont.

gggaccaacg gggcgcctgc ggattcacca tgccaaactg gcccaggctg gcgcttacca
gtgcattgtg gacaatgggg tggcgcctcc agcacgacgg ctgctccgtc ttgttgtcag
atttgccccc caggtggagc accccactcc cctaactaag gtggctgcag ctggagacag
caccagttct gccaccctcc actgccgtgc ccgaggtgtc cccaacatcg ttttcacttg
gacaaaaaac ggggtccctc tggatctcca agatcccagg tacacggagc acacatacca
ccagggtggt gtccacagca gcctcctgac cattgccaac gtgtctgccg cccaggatta
cgccctcttc acatgtacag ccaccaacgc ccttggctcg gaccaaacca acattcaact
tgtcagcatc agccgccctg accctccatc aggattaaag gttgtgagtc tgaccccaca
ctccgtgggg ctggagtgga agcctggctt tgatgggggc tgccacaga ggttctgcat
caggtatgag gccctgggga ctccagggtt ccactatgtg gatgtcgtac caccccaggc
caccaccttc acgctgactg gtctacagcc ttctacaaga tacagggtct ggctgctggc
cagtaatgcc ttgggggaca gtggactggc tgacaaaggg acccagcttc ccatcactac
cccaggtctc caccagcctt ctggagaacc tgaagaccag ctgcccacag agccaccttc
aggaccctcg gggctgcccc tgctgcctgt gctgttcgct cttgggggggc ttctgctcct ctccaatgcc
tcctgtgtcg ggggggtcct ctggcagcgg agactcaggc gtcttgctga gggcatctca
gagaagacag aggcagggtc ggaagaggac cgagtcagga acgaatatga ggagagccag
tggacaggag agcgggacac tcagagctcc acggtcagca caacagaggc agagccgtat
taccgctccc tgagggactt cagcccccag ctgccccga cgcaggagga ggtgtcttat
tcccgaggtt tcacaggtga agatgaggat atggccttcc ctgggcactt gtatgatgag
gtagaaagaa cgtaccccc gtctggagcc tggggacccc tctacgatga agtgcagatg
ggaccctggg acctccactg gcctgaagac acatatcagg atccaagagg aatctatgac
caggtggccg gagacttgga cactctggaa cccgattctc tgcccttcga gctgagggga
catctggtgt aagagccctc tcaaccccat tgtcctgcac ctgcaggaat ttacactcca ctggtctctc
tcattacagc ctgggccgag ctggttaggt gagctccata aaacccaaag ggacttggtg
tcaggagagg acatggaggg ggctgagtga cagagatggt tcagctggta ccagagtaga
aacaaggtgc atcctggggt tggctttaga aactaaactt ctccaaaagg acagggcaga
ttgtaaacgt cgtctcaaaa atgaaatgct gccgggtgcg gtgactcacg cctataatcc
cagcactttg ggaggctgag gcgggtggat cacctgaggt caggagttcg agaccagcct
ggccaacatg gtaaaactcc atttctacta aaatataaa aaattagcca ggagtagtgg
cgcatgcctg tagtcccagc tacttgggag gctgatgcat gagaattgct tgaacccagg
aggcggaggt tgcagtgagc tgagatcacg ccactgcact ccagcctggg cgacagagcg
agattctgtc tcaaaaaata aaataaaat aaaataaaa aataaaatgc tattctgagg
gtccctaagt gcttcatgaa gtaaagtttt cagaagtggg gaaagacata tgaaaaactc
tgttcatttt gcattccatg acgtctgaaa tagctaataa taagtggaat ttatgaatcc atgttgcatc
ctacctatta ttttattatt tccgacagtt atctaacaca ggaggcataa actatgacac atgtaaacat
aagtatgctc cataagcatt aaaataaaca gacaatcaaa agaagctaga ggaaaagaat
atgtactgtg tgtgtgcttt cgtttataga aattctaaaa taggcaaaac taatctacgg
tggcagagag cacagcagag gtttcctggg gccatgagag gagggttgac tgcaaaaagg
catgggagaa ctttctgagg tgttggaaat attctatata acgattgtgg tggtggttgc
acgggtgcac agatttgtca aaactcattg aactttacac ttaagatggg tgcattttta ttgtacataa
atgatatctc aataaaagtg attttaaaaa cagg

SEQ ID NO: 4

Fig. 4B gagaatgagc tcaagctggg tcagagagca gggctgactc tgccagtgcc tgcatcagcc tcatcgctct
cctaggctcc tggcctgctg gactctgggc tgcaggtcct tcttgaaagg ctgtgagtag tgagacaagg
agcaggagtg aggggtggca ggagagaaga tagagattga gagagagaga gagagagaga cagagagaga
ggaagagaca gagacaaaag gagagagaac ggcttagaca aggagagaaa gatggaaaga taaagagact
gggcgcagtg gctcacgcct gtaatcccaa cacttgggga ggccaaggtg ggaggatggc ttgaaggaaa
gagtctgaga tcaacctggc caacatagtg agacccgtc tctaaaaaaa aaaaaagaa aaaaaaaga
aaaaagaaaa aaaagttttt ttaaagagac agagaaagag actcagagat tgagactgag agcaagacag
agagagatac tcacagggaa gaggggaaga ggaaaacgag aaagggagga gagtaacgga aagagataaa
aaagaaaagc aggtggcaga gacacacaga gagggaccca gagaaagcca gacagacgca ggtggctggc
agcgggcgct gtgggggtca cagtaggggg acctgtgatg gccctgggga cgacgctcag ggcttctctc
ctgctcctgg ggctgctgac tgaaggcctg gcgcagttgg cgattcctgc ctccgttccc cggggcttct
gggccctgcc tgaaaacctg acggtggtgg aggggcctc agtggagctg cgttgtgggg tcagcacccc
tggcagtgcg gtgcaatggg ccaaagatgg gctgctcctg gccccgacc ccaggatccc aggcttccg
aggtaccgcc tggaagggga ccctgctaga ggtgaattcc acctgcacat cgaggcctgt gacctcagcg
atgacgcgga gtatgagtgc caggtcggcc gctctgagat ggggcccgag ctcgtgtctc ccagagtgat
cctctccatc ctggttcctc ccaagctgct cctgctgacc cagaggcag gcaccatggt cacctgggta
gctgggcagg agtacgtggt caactgtgtg tctggggacg cgaagccagc acctgacatc accattctcc
tgagtggaca gacaatatct gacatctctg caaacgtgaa cgagggctcc cagcagaaac tcttcactgt
ggaggccaca gccagggtga caccccggag ctcagataat aggcagttgc tggtctgtga ggcgtctagc
ccagcactgg aggcccccat caaggcctca ttcaccgtga atgttctgtt ccctccagga cccctgtca
tcgagtggcc aggcctggat gaggggcacg tgcgggcagg acagagcttg gagctgccgt gcgtggcccg
aggggggtaat cccttagcca cactgcagtg gctgaagaat ggccagccgg tgtccacagc gtggggcaca
gagcacaccc aggcggtggc ccgcagtgtg ctggtgatga ccgtgaggcc agaagaccat ggagcgcagc
tcagctgcga ggcccacaac agcgtgtctg cagggaccca ggagcacggc atcacactgc aggtcaccctt
tcccctagt gccattatta tcttgggatc tgcatcccag actgagaaca agaacgtgac actctcctgt
gtcagcaagt ccagtcgccc gcgggttctg ctacgatggt ggctgggctg gcggcagctg ctgcccatgg
aggagacagt catggatgga ctgcatggcg gtcacatctc catgtccaac ctgacattcc tggcgcggcg
ggaggacaac ggtctgaccc tcacatgtga ggccttcagt gaagccttca ccaaggagac cttcaagaag
tcgctcatcc tgaacgtaaa atatcccgcc cagaaactgt ggattgaggg tcccccagag ggccagaagc
tccgggctgg gacccgggtg aggctggtgt gtttggctat cgggggcaac ccagagccct ccctcatgtg
gtacaaggac tcgcgcaccg tgaccgagtc gcggctgccg caggagtcgc ggcgcgtgca tctcggcagc
gtgggagaaat ctgggagcac cttctcccga gagctggtgc tggtcacagg gccgtcggac aaccaggcca
agttcacgtg caaggctgga cagctcagcg cgtccacgca gctggcggtg cagtttcccc caactaacgt
gacgatcctg gccaacgcat ccgcactgcg cccgggagac gccttaaact tgacatgcgt cagcgtcagc
agcaatccgc cggtcaactt gtcctgggac aaggaagggg agaggctgga gggcgtggcc gccccacccc
ggagagcccc attcaaaggc tccgccgccg ccaggagcgt ccttctgcaa gtgtcatccc gcgatcatgg
ccagcgcgtg acctgccgcg cccacagcgc cgagctccgc gaaaccgtga gctccttcta tcgcctcaac
gtactgtacc gtccagagtt cctgggggag caggtgctgg tggtgaccgc ggtggagcag ggcgaggcgt
tgctgcccgt gtccgtgtcc gctaacccg cccccgaggc cttcaactgg accttccgcg gctatcgcct
cagtccagcg ggcggccccc ggcatcgcat

Fig. 4B cont.

cctgtccagc gggggctctgc atctgtggaa tgtgacccgc gcggacgacg gcctctatca gctgcactgc
cagaactctg agggcaccgc ggaagcgcgg ctgcggctgg acgtgcacta tgctcccacc atccgtgccc
tccaggaccc cactgaggtg aacgtcgggg gttctgtgga catagtctgc actgtcgatg ccaatcccat
cctcccgggc atgttcaact gggagagact gggagaagat gaggaggacc agagcctgga tgacatggag
aagatatcca ggggaccaac ggggcgcctg cggattcacc atgccaaact ggcccaggct ggcgcttacc
agtgcattgt ggacaatggg gtggcgcctc cagcacgacg gctgctccgt cttgttgtca gatttgcccc
ccaggtggag caccccactc ccctaactaa ggtggctgca gctggagaca gcaccagttc tgccaccctc
cactgccgtg cccgaggtgt ccccaacatc gttttcactt ggacaaaaaa cggggtccct ctggatctcc
aagatcccag gtacacggag cacacatacc accagggtgg tgtccacagc agcctcctga ccattgccaa
cgtgtctgcc gcccaggatt acgccctctt cacatgtaca gccaccaacg cccttggctc ggaccaaacc
aacattcaac ttgtcagcat cagccgcccct gaccctccat caggattaaa ggttgtgagt ctgaccccac
actccgtggg gctggagtgg aagcctggct tgatggggg cctgccacag aggttctgca tcaggtatga
ggccctgggg actccagggt tccactatgt ggatgtcgta ccaccccagg ccaccacctt cacgctgact
ggtctacagc cttctacaag atacagggtc tggctgctgg ccagtaatgc cttgggggac agtggactgg
ctgacaaagg gacccagctt cccatcacta ccccaggtct ccaccagcct tctggagaac ctgaagacca
gctgcccaca gagccacctt caggaccctc ggggctgccc ctgctgcctg tgctgttcgc tcttgggggg
cttctgctcc tctccaatgc ctcctgtgtc gggggggtcc tctggcagcg gagactcagg cgtcttgctg
agggcatctc agagaagaca gaggcagggt cggaagagga ccgagtcagg aacgaatatg
aggagagcca gtggacagga gagcgggaca ctcagagctc cacggtcagc acaacagagg
cagagccgta ttaccgctcc ctgagggact tcagccccca gctgccccg acgcaggagg aggtgtctta
ttcccgaggt ttcacaggtg aagatgagga tatggccttc cctgggcact tgtatgatga ggtagaaaga
acgtaccccc cgtctggagc ctggggaccc ctctacgatg aagtgcagat gggaccctgg gacctccact
ggcctgaaga cacatatcag gatccaagag gaatctatga ccaggtggcc ggagacttgg acactctgga
acccgattct ctgcccttcg agctgagggg acatctggtg taagagccct ctcaacccca ttgtcctgca
cctgcaggaa tttacactcc actggtctct ctcattacag cctgggccga gctggttagg tgagctccat
aaaacccaaa gggacttggt gtcaggagag gacatggagg gggctgagtg acagagatgg ttcagctggt
accagagtag aaacaaggtg catcctgggg ttggctttag aaactaaact tctccaaaag gacagggcag
attgtaaacg tcgtctcaaa aatgaaatgc tgccgggtgc ggtgactcac gcctataatc ccagcacttt
gggaggctga ggcgggtgga tcacctgagg tcaggagttc gagaccagcc tggccaacat ggtaaaactc
catttctact aaaaatataa aaattagcc aggagtagtg gcgcatgcct gtagtcccag ctacttggga
ggctgatgca tgagaattgc ttgaacccag gaggcggagg ttgcagtgag ctgagatcac gccactgcac
tccagcctgg gcgacagagc gagattctgt ctcaaaaaat aaaaataaaa taaaaataaa aataaaatg
ctattctgag ggtccctaag tgcttcatga agtaaagttt tcagaagtgg ggaaagacat atgaaaact
ctgttcattt tgcattccat gacgtctgaa atagctaata ataagtggaa tttatgaatc catgttgcat
cctacctatt attttattat ttccgacagt tatctaacac aggaggcata aactatgaca catgtaaaca
taagtatgct ccataagcat taaataaac agacaatcaa agaagctag aggaaaagaa tatgtactgt
gtgtgtgctt tcgtttatag aaattctaaa ataggcaaaa ctaatctacg gtggcagaga gcacagcaga
ggtttcctgg ggccatgaga ggagggttga ctgcaaaaag gcatgggaga actttctgag gtgttggaaa
tattctatat aacgattgtg gtggtggttg cacgggtgca cagatttgtc aaaactcatt gaactttaca
cttaagatgg gtgcattttt attgtacata aatgatatct caataaaagt gattttaaaa acagg

SEQ ID NO: 5

SEQUENCE LISTING

```
<160> NUMBER OF SEQ ID NOS: 5

<210> SEQ ID NO 1
<211> LENGTH: 1192
<212> TYPE: DNA
<213> ORGANISM: Artificial Sequence
<220> FEATURE:
<223> OTHER INFORMATION: Synthetic

<400> SEQUENCE: 1
cacctgaggt caggagttcg agaccagcgt ggccaacatg atgaaacccc gtctctagta      60
aaaatacaaa aattagccag gcatggtgct atatacctgt agcaccagct acttgggaga     120
cagaggtggg agaattactt gaacctggga ggttcaagcc atgggaggtg gaagttgcag     180
tgagccgaga tgccactgca ctccagcctg agcaacagag caagactatc tcaagaaaag     240
aaagaaagaa agaaagagac ttgccaaggt catgtatcag ggcaaggaag agctgggggc     300
ccagctggct gctcccctgc tgagctggga gaccaccttg atctgacttc tcccatcttc     360
ccagcctaag ccaggccctg gggtcacgga ggctggggag gcaccgagga acgcgcctgg     420
catgtgctga caggggattt tatgctccag ctgggccagc tgggaggagc ctgctgggca     480
gaggccagag ctgggggctc tggaaggtac ctgggggagg ttgcactgtg agaatgagct     540
caagctgggt cagagagcag ggctgactct gccagtgcct gcatcagcct catcgctctc     600
ctaggctcct ggcctgctgg actctgggct gcaggtcctt cttgaaaggc tgtgagtagt     660
gagacaagga gcaggagtga ggggtggcag gagagaagat agagattgag agagagagag     720
agagagagac agagagagag gaagagacag agacaaaagg agagagaacg gcttagacaa     780
ggagagaaag atggaaagat aaagagactg ggcgcagtgg ctcacgcctg taatcccaac     840
acttggggag gccaaggtgg gaggatggct tgaaggaaag agtctgagat caacctggcc     900
aacatagtga gaccccgtct ctaaaaaaaa aagaaaaaaa aaagaaaaaa gaaaaaaaag     960
tttttttaaa gagacagaga aagagactca gagattgaga ctgagagcaa gacagagaga    1020
gatactcaca gggaagaggg gaagaggaaa acgaaaaggg gaggagagta acggaaagag    1080
ataaaaaaga aaagcaggtg gcagagacac acagagaggg acccagagaa agccagacag    1140
acgcaggtgg ctggcagcgg gcgctgtggg ggtcacagta gggggacctg tg             1192

<210> SEQ ID NO 2
<211> LENGTH: 589
<212> TYPE: DNA
<213> ORGANISM: Artificial Sequence
<220> FEATURE:
<223> OTHER INFORMATION: Synthetic

<400> SEQUENCE: 2
```

| | |
|---|---:|
| aatcaacctc tggattacaa aatttgtgaa agattgactg gtattcttaa ctatgttgct | 60 |
| ccttttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccact | 240 |
| ggttggggca ttgccaccac ctgtcagctc ctttccggga ctttcgcttt ccccctccct | 300 |
| attgccacgg cggaactcat cgccgcctgc cttgcccgct gctggacagg gctcggctg | 360 |
| ttgggcactg acaattccgt ggtgttgtcg gggaaatcat cgtcctttcc ttggctgctc | 420 |
| gcctgtgttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 3
<211> LENGTH: 225
<212> TYPE: DNA
<213> ORGANISM: Artificial Sequence
<220> FEATURE:
<223> OTHER INFORMATION: Synthetic

<400> SEQUENCE: 3

| | |
|---|---:|
| ctgtgccttc tagttgccag ccatctgttg tttgcccctc cccgtgcct tccttgaccc | 60 |
| tggaaggtgc cactcccact gtcctttcct aataaaatga ggaaattgca tcgcattgtc | 120 |
| tgagtaggtg tcattctatt ctgggggtg gggtggggca ggacagcaag ggggaggatt | 180 |
| gggaagacaa tagcaggcat gctggggatg cggtgggctc tatgg | 225 |

<210> SEQ ID NO 4
<211> LENGTH: 5024
<212> TYPE: DNA
<213> ORGANISM: Artificial Sequence
<220> FEATURE:
<223> OTHER INFORMATION: Synthetic

<400> SEQUENCE: 4

| | |
|---|---:|
| aggggaagag gaaaacgaga aagggaggag agtaacggaa agagataaaa aagaaaagca | 60 |
| ggtggcagag acacacagag agggacccag agaaagccag acagacgcag gtggctggca | 120 |
| gcgggcgctg tggggtcac agtaggggga cctgtgatgg ccctggggac gacgctcagg | 180 |
| gcttctctcc tgctcctggg gctgctgact gaaggcctgg cgcagttggc gattcctgcc | 240 |
| tccgttcccc ggggcttctg ggccctgcct gaaaacctga cggtggtgga ggggcctca | 300 |
| gtggagctgc gttgtggggt cagcaccccct ggcagtgcgg tgcaatgggc caaagatggg | 360 |
| ctgctcctgg gccccgaccc caggatccca ggcttcccga ggtaccgcct ggaagggac | 420 |
| cctgctagag gtgaattcca cctgcacatc gaggcctgtg acctcagcga tgacgcggag | 480 |
| tatgagtgcc aggtcggccg ctctgagatg ggggcccgagc tcgtgtctcc cagagtgatc | 540 |
| ctctccatcc tggttcctcc caagctgctc ctgctgaccc cagaggcagg caccatggtc | 600 |
| acctgggtag ctgggcagga gtacgtggtc aactgtgtgt ctgggacgc gaagccagca | 660 |
| cctgacatca ccattctcct gagtggacag acaatatctg acatctctgc aaacgtgaac | 720 |
| gagggctccc agcagaaact cttcactgtg gaggccacag ccagggtgac accccggagc | 780 |
| tcagataata ggcagttgct ggtctgtgag gcgtctagcc cagcactgga ggccccccatc | 840 |
| aaggcctcat tcaccgtgaa tgttctgttc cctccaggac ccctgtcat cgagtggcca | 900 |
| ggcctggatg aggggcacgt gcgggcagga cagagcttgg agctgccgtg cgtggcccga | 960 |

```
gggggtaatc ccttagccac actgcagtgg ctgaagaatg ccagccggt gtccacagcg    1020 tggggcacag agcacaccca ggcggtggcc cgcagtgtgc tggtgatgac cgtgaggcca    1080
gaagaccatg gagcgcagct cagctgcgag gcccacaaca gcgtgtctgc agggacccag    1140
gagcacggca tcacactgca ggtcaccttt cccctagtg ccattattat cttgggatct    1200
gcatcccaga ctgagaacaa gaacgtgaca ctctcctgtg tcagcaagtc cagtcgcccg    1260
cgggttctgc tacgatggtg gctgggctgg cggcagctgc tgcccatgga ggagacagtc    1320
atggatggac tgcatggcgg tcacatctcc atgtccaacc tgacattcct ggcgcggcgg    1380
gaggacaacg gtctgaccct cacatgtgag gccttcagtg aagccttcac caaggagacc    1440
ttcaagaagt cgctcatcct gaacgtaaaa tatcccgccc agaaactgtg gattgagggt    1500
cccccagagg gccagaagct ccgggctggg accgggtga ggctggtgtg tttggctatc    1560 ggggcaacc cagagccctc cctcatgtgg tacaaggact cgcgcaccgt gaccgagtcg    1620
cggctgccgc aggagtcgcg gcgcgtgcat ctcggcagcg tggagaaatc tgggagcacc    1680
ttctcccgag agctggtgct ggtcacaggg ccgtcggaca accaggccaa gttcacgtgc    1740
aaggctggac agctcagcgc gtccacgcag ctggcggtgc agtttcccc aactaacgtg    1800 acgatcctgg ccaacgcatc cgcactgcgc ccgggagacg ccttaaactt gacatgcgtc    1860
agcgtcagca gcaatccgcc ggtcaacttg tcctgggaca aggaagggga gaggctggag    1920
ggcgtggccg ccccacccg gagagcccca ttcaaaggct ccgccgccgc caggagcgtc    1980
cttctgcaag tgtcatcccg cgatcatggc cagcgcgtga cctgccgcgc ccacagcgcc    2040
gagctccgcg aaaccgtgag ctccttctat cgcctcaacg tactgtaccg tccagagttc    2100 ctggggagc aggtgctggt ggtgaccgcg gtggagcagg cgaggcgtt gctgcccgtg    2160 tccgtgtccg ctaaccccgc ccccgaggcc ttcaactgga ccttccgcgg ctatcgcctc    2220
agtccagcgg gcggccccg gcatcgcatc ctgtccagcg gggctctgca tctgtggaat    2280
gtgacccgcg cggacgacgg cctctatcag ctgcactgcc agaactctga gggcaccgcg    2340
gaagcgcggc tgcggctgga cgtgcactat gctcccacca tccgtgccct ccaggacccc    2400
actgaggtga acgtcggggg ttctgtggac atagtctgca ctgtcgatgc caatcccatc    2460
ctcccgggca tgttcaactg ggagagactg ggagaagatg aggaggacca gagcctggat    2520
gacatggaga agatatccag gggaccaacg gggcgcctgc ggattcacca tgccaaactg    2580
gcccaggctg gcgcttacca gtgcattgtg gacaatgggg tggcgcctcc agcacgacgg    2640
ctgctccgtc ttgttgtcag atttgccccc caggtggagc accccactcc cctaactaag    2700
gtggctgcag ctggagacag caccagttct gccaccctcc actgccgtgc ccgaggtgtc    2760
cccaacatcg ttttcacttg gacaaaaaac ggggtccctc tggatctcca agatcccagg    2820
tacacggagc acacatacca ccagggtggt gtccacagca gcctcctgac cattgccaac    2880
gtgtctgccg cccaggatta cgccctcttc acatgtacag ccaccaacgc ccttggctcg    2940
gaccaaacca acattcaact tgtcagcatc agccgccctg accctccatc aggattaaag    3000
gttgtgagtc tgacccccaca ctccgtgggg ctggagtgga agcctggctt tgatggggc    3060 ctgccacaga ggttctgcat caggtatgag gccctgggga ctccagggtt ccactatgtg    3120
gatgtcgtac caccccaggc caccaccttc acgctgactg gtctacagcc ttctacaaga    3180
tacagggtct ggctgctggc cagtaatgcc ttggggggaca gtggactggc tgacaaaggg    3240
acccagcttc ccatcactac cccaggtctc caccagcctt ctggagaacc tgaagaccag    3300
```

| | |
|---|---|
| ctgcccacag agccaccttc aggaccctcg gggctgcccc tgctgcctgt gctgttcgct | 3360 |
| cttgggggc ttctgctcct ctccaatgcc tcctgtgtcg gggggtcct ctggcagcgg | 3420 |
| agactcaggc gtcttgctga gggcatctca gagaagacag aggcagggtc ggaagaggac | 3480 |
| cgagtcagga acgaatatga ggagagccag tggacaggag agcgggacac tcagagctcc | 3540 |
| acggtcagca aacagaggc agagccgtat taccgctccc tgagggactt cagccccag | 3600 |
| ctgccccga cgcaggagga ggtgtcttat tcccgaggtt tcacaggtga agatgaggat | 3660 |
| atggccttcc ctgggcactt gtatgatgag gtagaaagaa cgtaccccc gtctggagcc | 3720 |
| tggggacccc tctacgatga agtgcagatg ggaccctggg acctccactg gcctgaagac | 3780 |
| acatatcagg atccaagagg aatctatgac caggtggccg gagacttgga cactctggaa | 3840 |
| cccgattctc tgcccttcga gctgagggga catctggtgt aagagccctc tcaaccccat | 3900 |
| tgtcctgcac ctgcaggaat ttacactcca ctggtctctc tcattacagc ctgggccgag | 3960 |
| ctggttaggt gagctccata aacccaaag ggacttggtg tcaggagagg acatggaggg | 4020 |
| ggctgagtga cagagatggt tcagctggta ccagagtaga aacaaggtgc atcctggggt | 4080 |
| tggctttaga aactaaactt ctccaaaagg acagggcaga ttgtaaacgt cgtctcaaaa | 4140 |
| atgaaatgct gccgggtgcg gtgactcacg cctataatcc cagcactttg ggaggctgag | 4200 |
| gcgggtggat cacctgaggt caggagttcg agaccagcct ggccaacatg gtaaaactcc | 4260 |
| atttctacta aaaatataaa aaattagcca ggagtagtgg cgcatgcctg tagtcccagc | 4320 |
| tacttgggag gctgatgcat gagaattgct tgaacccagg aggcggaggt tgcagtgagc | 4380 |
| tgagatcacg ccactgcact ccagcctggg cgacagagcg agattctgtc tcaaaaaata | 4440 |
| aaaataaaat aaaaataaaa aataaaatgc tattctgagg gtccctaagt gcttcatgaa | 4500 |
| gtaaagtttt cagaagtggg gaaagacata tgaaaaactc tgttcatttt gcattccatg | 4560 |
| acgtctgaaa tagctaataa taagtggaat ttatgaatcc atgttgcatc ctacctatta | 4620 |
| ttttattatt tccgacagtt atctaacaca ggaggcataa actatgacac atgtaaacat | 4680 |
| aagtatgctc cataagcatt aaaataaaca gacaatcaaa agaagctaga ggaaaagaat | 4740 |
| atgtactgtg tgtgtgctttt cgtttataga aattctaaaa taggcaaaac taatctacgg | 4800 |
| tggcagagag cacagcagag gtttcctggg gccatgagag gagggttgac tgcaaaaagg | 4860 |
| catgggagaa ctttctgagg tgttggaaat attctatata acgattgtgg tggtggttgc | 4920 |
| acgggtgcac agatttgtca aaactcattg aactttacac ttaagatggg tgcatttttta | 4980 |
| ttgtacataa atgatatctc aataaaagtg attttaaaaa cagg | 5024 |

```
<210> SEQ ID NO 5
<211> LENGTH: 5535
<212> TYPE: DNA
<213> ORGANISM: Artificial Sequence
<220> FEATURE:
<223> OTHER INFORMATION: Synthetic

<400> SEQUENCE: 5
```

| | |
|---|---|
| gagaatgagc tcaagctggg tcagagagca gggctgactc tgccagtgcc tgcatcagcc | 60 |
| tcatcgctct cctaggctcc tggcctgctg gactctgggc tgcaggtcct tcttgaaagg | 120 |
| ctgtgagtag tgagacaagg agcaggagtg aggggtggca ggagagaaga tagagattga | 180 |
| gagagagaga gagagagaga cagagagaga ggaagagaca gagacaaaag gagagagaac | 240 |
| ggcttagaca aggagagaaa gatggaaaga taaagagact gggcgcagtg gctcacgcct | 300 |
| gtaatcccaa cacttgggga ggccaaggtg ggaggatggc ttgaaggaaa gagtctgaga | 360 |

```
tcaacctggc caacatagtg agaccccgtc tctaaaaaaa aaaaaaagaa aaaaaaaga      420 aaaaagaaaa aaaagttttt ttaaagagac agagaaagag actcagagat tgagactgag      480
agcaagacag agagagatac tcacagggaa gaggggaaga ggaaaacgag aaagggagga      540
gagtaacgga aagagataaa aaagaaaagc aggtggcaga gacacacaga gagggaccca      600
gagaaagcca gacagacgca ggtggctggc agcgggcgct gtggggtca cagtaggggg       660 acctgtgatg gccctgggga cgacgctcag ggcttctctc ctgctcctgg ggctgctgac      720
tgaaggcctg gcgcagttgg cgattcctgc ctccgttccc cggggcttct gggccctgcc      780
tgaaaacctg acgtggtgg aggggcctc agtggagctg cgttgtgggg tcagcacccc       840
tggcagtgcg gtgcaatggg ccaaagatgg gctgctcctg gccccgacc ccaggatccc       900 aggcttcccg aggtaccgcc tggaagggga ccctgctaga ggtgaattcc acctgcacat      960
cgaggcctgt gacctcagcg atgacgcgga gtatgagtgc caggtcggcc gctctgagat     1020
ggggcccgag ctcgtgtctc ccagagtgat cctctccatc ctggttcctc caagctgct    1080 cctgctgacc ccagaggcag gcaccatggt cacctgggta gctgggcagg agtacgtggt    1140
caactgtgtg tctggggacg cgaagccagc acctgacatc accattctcc tgagtggaca    1200
gacaatatct gacatctctg caaacgtgaa cgagggctcc cagcagaaac tcttcactgt    1260
ggaggccaca gccagggtga caccccggag ctcagataat aggcagttgc tggtctgtga    1320
ggcgtctagc ccagcactgg aggcccccat caaggcctca ttcaccgtga atgttctgtt    1380
ccctccagga ccccctgtca tcgagtggcc aggcctggat gaggggcacg tgcgggcagg    1440
acagagcttg gagctgccgt gcgtggcccg aggggggtaat cccttagcca cactgcagtg    1500
gctgaagaat ggccagccgg tgtccacagc gtggggcaca gagcacaccc aggcggtggc    1560
ccgcagtgtg ctggtgatga ccgtgaggcc agaagaccat ggagcgcagc tcagctgcga    1620
ggcccacaac agcgtgtctg cagggaccca ggagcacggc atcacactgc aggtcacctt    1680 tcccccctagt gccattatta tcttgggatc tgcatcccag actgagaaca agaacgtgac    1740
actctcctgt gtcagcaagt ccagtcgccc gcgggttctg ctacgatggt ggctgggctg    1800
gcggcagctg ctgcccatgg aggagacagt catggatgga ctgcatggcg gtcacatctc    1860
catgtccaac ctgacattcc tggcgcggcg ggaggacaac ggtctgaccc tcacatgtga    1920
ggccttcagt gaagccttca ccaaggagac cttcaagaag tcgctcatcc tgaacgtaaa    1980
atatcccgcc cagaaactgt ggattgaggg tcccccagag ggccagaagc tccgggctgg    2040
gacccgggtg aggctggtgt gtttggctat cggggggcaac ccagagccct ccctcatgtg    2100
gtacaaggac tcgcgcaccg tgaccgagtc gcggctgccg caggagtcgc ggcgcgtgca    2160
tctcggcagc gtggagaaat ctgggagcac cttctcccga gagctggtgc tggtcacagg    2220
gccgtcggac aaccaggcca agttcacgtg caaggctgga cagctcagcg cgtccacgca    2280
gctggcggtc cagtttcccc caactaacgt gacgatcctg ccaacgcat ccgcactgcg    2340 cccgggagac gccttaaaact tgacatgcgt cagcgtcagc agcaatccgc cggtcaactt    2400
gtcctgggac aaggaagggg agaggctgga gggcgtggcc gccccacccc ggagagcccc    2460
attcaaaggc tccgccgccg ccaggagcgt ccttctgcaa gtgtcatccc gcgatcatgg    2520
ccagcgcgtg acctgccgcg cccacagcgc cgagctccgc gaaaccgtga gctccttcta    2580
tcgcctcaac gtactgtacc gtccagagtt cctggggggag caggtgctgg tggtgaccgc    2640
ggtggagcag ggcgaggcgt tgctgcccgt gtccgtgtcc gctaacccg ccccgaggc    2700
```

```
cttcaactgg accttccgcg gctatcgcct cagtccagcg ggcggccccc ggcatcgcat    2760
cctgtccagc ggggctctgc atctgtggaa tgtgacccgc gcggacgacg gcctctatca    2820
gctgcactgc cagaactctg agggcaccgc ggaagcgcgg ctgcggctgg acgtgcacta    2880
tgctcccacc atccgtgccc tccaggaccc cactgaggtg aacgtcgggg gttctgtgga    2940
catagtctgc actgtcgatg ccaatcccat cctcccgggc atgttcaact gggagagact    3000
gggagaagat gaggaggacc agagcctgga tgacatggag aagatatcca ggggaccaac    3060
ggggcgcctg cggattcacc atgccaaact ggcccaggct ggcgcttacc agtgcattgt    3120
ggacaatggg gtggcgcctc cagcacgacg gctgctccgt cttgttgtca gatttgcccc    3180
ccaggtggag cacccccactc ccctaactaa ggtggctgca gctggagaca gcaccagttc    3240
tgccaccctc cactgccgtg cccgaggtgt cccaacatc gttttcactt ggacaaaaaa    3300
cggggtccct ctggatctcc aagatcccag gtacacggag cacacatacc accagggtgg    3360
tgtccacagc agcctcctga ccattgccaa cgtgtctgcc gcccaggatt acgccctctt    3420
cacatgtaca gccaccaacg cccttggctc ggaccaaacc aacattcaac ttgtcagcat    3480
cagccgccct gaccctccat caggattaaa ggttgtgagt ctgaccccac actccgtggg    3540
gctggagtgg aagcctggct ttgatggggg cctgccacag aggttctgca tcaggtatga    3600
ggccctgggg actccagggt tccactatgt ggatgtcgta ccacccccagg ccaccacctt    3660 cacgctgact ggtctacagc cttctacaag atacaggggtc tggctgctgg ccagtaatgc    3720
cttgggggac agtggactgg ctgacaaagg gacccagctt cccatcacta ccccaggtct    3780
ccaccagcct tctggagaac ctgaagacca gctgcccaca gagccacctt caggaccctc    3840
ggggctgccc ctgctgcctg tgctgttcgc tcttgggggg cttctgctcc tctccaatgc    3900
ctcctgtgtc gggggggtcc tctggcagcg gagactcagg cgtcttgctg agggcatctc    3960
agagaagaca gaggcagggt cggaagagga ccgagtcagg aacgaatatg aggagagcca    4020
gtggacagga gagcgggaca ctcagagctc cacggtcagc acaacagagg cagagccgta    4080
ttaccgctcc ctgagggact tcagccccca gctgccccg acgcaggagg aggtgtctta    4140
ttcccgaggt ttcacaggtg aagatgagga tatggccttc cctgggcact tgtatgatga    4200
ggtagaaaga acgtaccccc cgtctggagc ctggggaccc ctctacgatg aagtgcagat    4260
gggaccctgg gacctccact ggcctgaaga cacatatcag gatccaagag gaatctatga    4320
ccaggtggcc ggagacttgg acactctgga acccgattct ctgcccttcg agctgagggg    4380
acatctggtg taagagccct ctcaaccccca ttgtcctgca cctgcaggaa tttacactcc    4440
actggtctct ctcattacag cctgggccga gctggttagg tgagctccat aaaacccaaa    4500
gggacttggt gtcaggagag gacatggagg gggctgagtg acagagatgg ttcagctggt    4560
accagagtag aaacaaggtg catcctgggg ttggctttag aaactaaact tctccaaaag    4620
gacagggcag attgtaaacg tcgtctcaaa aatgaaatgc tgccgggtgc ggtgactcac    4680
gcctataatc ccagcacttt gggaggctga ggcgggtgga tcacctgagg tcaggagttc    4740
gagaccagcc tggccaacat ggtaaaactc catttctact aaaaatataa aaaattagcc    4800
aggagtagtg gcgcatgcct gtagtcccag ctacttggga ggctgatgca tgagaattgc    4860
ttgaacccag gaggcggagg ttgcagtgag ctgagatcac gccactgcac tccagcctgg    4920
gcgacagagc gagattctgt ctcaaaaaat aaaaataaaa taaaaataaa aataaaatg    4980 ctattctgag ggtccctaag tgcttcatga agtaaagttt tcagaagtgg ggaaagacat    5040
atgaaaaact ctgttcattt tgcattccat gacgtctgaa atagctaata ataagtggaa    5100
```

```
tttatgaatc catgttgcat cctacctatt attttattat ttccgacagt tatctaacac    5160
aggaggcata aactatgaca catgtaaaca taagtatgct ccataagcat taaaataaac    5220
agacaatcaa aagaagctag aggaaaagaa tatgtactgt gtgtgtgctt tcgtttatag    5280
aaattctaaa ataggcaaaa ctaatctacg gtggcagaga gcacagcaga ggtttcctgg    5340
ggccatgaga ggagggttga ctgcaaaaag gcatgggaga actttctgag gtgttggaaa    5400
tattctatat aacgattgtg gtggtggttg cacgggtgca cagatttgtc aaaactcatt    5460
gaactttaca cttaagatgg gtgcattttt attgtacata aatgatatct caataaaagt    5520
gattttaaaa acagg                                                    5535
```

THERAPY

CROSS-REFERENCE TO RELATED APPLICATIONS

This application claims priority to Great Britain Application No. GB2009039.5, filed Jun. 15, 2020.

Incorporation by Reference of Material Submitted Electronically

This application contains, as a separate part of the disclosure, a Sequence Listing in computer-readable form which is incorporated by reference in its entirety and identified as follows: Filename: 56901_Seglisting.txt; Size 17,188 bytes; Created: Jun. 15, 2021.

FIELD OF INVENTION

The present invention relates to gene therapies for use in treating monogenic forms of nephrotic syndrome

BACKGROUND TO THE INVENTION

Nephrotic syndrome (NS) is a chronic kidney disease characterized by significant proteinuria, hypoalbuminemia, oedema and hyperlipidemia, and is the most common primary glomerular disease in children, affecting 2/100,000 children below the age of 16 in Europe and the USA. NS is associated with different ages of onset, from less than 3 months old at diagnosis to early adulthood, and is classified in different patients groups depending on their sensitivity to corticoids: ~80% of children with NS are classified as having steroid-sensitive nephrotic syndrome (SSNS) and can be successfully treated with corticosteroid therapy. A proportion of patients originally classified as SSNS relapse and need further steroid treatment, and a further 10-15% of NS patients do not achieve remission after weeks of therapy with corticosteroids and are classified as having steroid-resistant nephrotic syndrome (SRNS). Up to 50% of these SRNS patients progress to end-stage renal disease within 10 years and commonly face an elevated risk of recurrence after renal transplant, highlighting the lack of suitable and efficient treatment for these patients.

Podocyte dysfunction and resultant disruption of the glomerular filtration barrier is central to the pathogenesis of NS. The podocyte branches off cellular processes to cover the outside of the glomerular capillary, called foot processes, and their interdigitations with neighbouring foot processes form the glomerular slit membrane, critical for the glomerular filtration barrier efficiency and for the retention of protein in the blood stream. In genetic forms of NS, mutations in genes coding for key podocyte processes such as the development, migration, basement membrane interaction, or regeneration of the podocyte, lead to the loss of integrity of the glomerular slit membrane and to the nephrotic syndrome phenotype. Approximately 30% of cases of SRNS in children are genetic, where the most common mutations in childhood are in NPHS2 encoding podocin, accounting for 10-30% of sporadic genetic cases.

Podocin is a 42 kDa hairpin like membrane-associated podocyte-specific protein that is a key component of the protein complex at the slit diaphragm; the cell-cell junction between adjacent podocyte foot processes. It localises to lipid rafts and interacts with other important slit diaphragm proteins like nephrin, CD2AP and TRPC6. It is essential in the maintenance of the slit diaphragm, and consequently the integrity of the glomerular filtration barrier. There are 126 mutations reported to date, but the most common mutation is R138Q, which causes mislocalisation of podocin to the endoplasmic reticulum.

As no effective treatment currently exists for patients with monogenic forms of NS, the use of gene therapy for the transfer of a functional gene copy in diseased podocytes could constitute a promising novel strategy to address monogenic forms of NS, reverse NS phenotype and correct kidney dysfunction. Indeed, US2003/0152954 generally suggested the use of viral vectors to deliver nucleic acids encoding polypeptides with podocin activity but failed to disclose or test any specific gene therapy constructs. It is likely that this is because the kidney has a complex anatomy with specialised compartments composed of glomeruli, tubules, vasculature, and interstitium, which makes it a difficult target for gene therapy vectors. To date renal-targeted gene therapy has been largely unsuccessful as the highly differentiated sub-structures of the kidney can be difficult to target and specifically transduce with viral vector approaches (van der Wouden et al., 2004).

A recent study attempted to target the kidney using rAAV vectors in combination with a CMV promoter and GFP or luciferase genes, which were administered via tail vein injection or renal vein injection (Rocca et al 2014). However, tail vein injection was shown to be unsuitable for kidney transduction and, while a low level of gene expression in podocytes was observed, widespread expression was also observed in the liver, despite the use of an allegedly kidney specific promoter. The study additionally failed to demonstrate successful transduction of a NS-associated transgene, such as podocin, and failed to demonstrate long term functional expression of such genes. The study also did not explore AAV serotypes suitable for human renal cell transduction.

The present invention aims to reverse the NS phenotype and correct podocyte-associated kidney dysfunction in patients with monogenic forms of NS by administering AAV gene therapy expressing a NS-associated transgene under the control of a podocyte-specific promoter.

SUMMARY OF THE INVENTION

The present invention provides an adeno-associated virus (AAV) vector gene therapy comprising a NS-associated transgene and minimal nephrin promoter NPHS1 or podocin promoter NPHS2, wherein the NS-associated transgene is selected from one or more of NPHS1, TRPC6, NUP107, NUP133, NUP160, ACTN4, INF2, ANKFY1, ANLN, CRB2, ITGA3, KANK1, KANK4, MAGI2, MYO1E, OCRL, PTPRO, SMARCAL1, SYNPO, TBC1D8B, XPO5, TNS2 or NLRP3. The gene therapy vector can be used to target podocytes within the glomerulus of the kidney in order to reverse the NS phenotype and correct podocyte-associated kidney dysfunction, particularly in patients with monogenic forms of NS.

Suitable AAV vector serotypes include 2/9, LK03 and 3B.

The AAV 2/9 serotype has shown significant tropism for newborn and adult mouse kidney, localising to the glomeruli and tubules (Luo et al., 2011; Picconi et al., 2014; Schievenbusch et al., 2010), and AAV2/9 vector combined with renal vein injection has been shown to be suitable for kidney-targeted gene delivery (Rocca et al., 2014). AAV 2/9 is therefore one suitable vector for use in the gene therapy of the present invention.

Synthetic AAV capsids such as LK03 can also be suitable vectors for use in the gene therapy of the present invention.

This vector has been shown to transduce human primary hepatocytes at high efficiency in vitro and in vivo. However, until now it has not been utilised in kidney-targeted gene delivery. Surprisingly, AAV-LK03 vectors can achieve high transduction of close to 100% in human podocytes in vitro and can be used to transduce podocytes specifically in vitro (see PCT/GB2020/050097, incorporated herein by reference).

The AAV-LK03 cap sequence consists of fragments from seven different wild-type serotypes (AAV1, 2, 3B, 4, 6, 8, 9), although AAV-3B represents 97.7% of the cap gene sequence and 98.9% of the amino acid sequence. AAV-3B is also known for its human hepatocyte tropism is another a suitable vector for use in the gene therapy of the present invention. To date it has not been utilised in kidney-targeted gene delivery.

The transgene species is preferably matched to the patient species. For example, when treating a human patient one would typically use a human transgene. The transgene may be naturally occurring, e.g. wild-type, or it may be recombinant. The transgene is typically included in the gene therapy vector as a cDNA sequence.

Use of a minimal nephrin promoter such as NPHS1 or podocin promoter NPHS2 allows the gene therapy vector to be targeted specifically to podocytes (Moeller et al., 2002; Picconi et al., 2014). This enables transgene expression to be specifically targeted to podocytes in the glomerular basement membrane of the kidney and minimises off-target expression. As podocytes are terminally differentiated and non-dividing cells they can be targeted for stable expression of the transgene and reduce or avoid any risk of vector dilution effect. In preferred embodiments of the invention the promoter is NPHS1. One example of a suitable DNA sequence for the NPHS1 promoter is shown in FIG. 1. The NPHS1 promoter may comprise a nucleic acid sequence which has at least 85%, 90%, 95%, 96%, 97%, 98%, 99% or more sequence identity to the sequence of FIG. 1, as long as it encodes a nephrin promoter that has retained its biological activity, particularly podocyte specific expression of a gene of interest or a reporter gene.

As with the transgene, the species of the promoter is preferably matched to the patient species. For example, when treating a human patient one would typically use human NHPS1 or human NPHS2.

The AAV vector may additionally comprise a Woodchuck hepatitis post-transcriptional regulatory element (WPRE). WPRE is a DNA sequence that, when transcribed, creates a tertiary structure enhancing expression. Inclusion of WPRE may increase expression of the transgene delivered by the vector. The WPRE sequence may be mutated to reduce oncogenicity without significant loss of RNA enhancement activity (Schambach et al., 2005, incorporated herein by reference). One example of a suitable WPRE sequence is shown in FIG. 2.

The NS-associated transgene may comprise a hemagglutinin (HA) tag. HA can be used as an epitope tag and has been shown not to interfere with bioactivity or biodistribution of proteins to which it has been added. The HA tag can facilitate detection, isolation, and purification of the transgene. Other suitable protein tags may include Myc tags, polyhistidine tags and flag tags.

The AAV vector may additionally comprise a Kozak sequence between the promoter and the podocin transgene. The Kozak sequence is known to play a major role in the initiation of the translation process and can therefore enhance expression of the NS-associated transgene.

The AAV vector may additionally comprise a polyadenylation signal, such as bovine growth hormone (bGH) polyadenylation signal, e.g., as shown in FIG. 3. Polyadenylation is the addition of a poly(A) tail to a messenger RNA. The poly(A) tail consists of multiple adenosine monophosphates; in other words, it is a stretch of RNA that has only adenine bases. The poly(A) tail is important for the nuclear export, translation, and stability of mRNA. Inclusion of a polyadenylation signal can therefore enhance expression of the NS-associated transgene.

The AAV vector gene therapy additionally typically comprises Inverted Terminal Repeat (ITR) sequences at either end of the vector. For example, the vector structure may be, in order: ITR-promotor-transgene (with optional HA tag)-optional WRPE-polyadenylation signal-ITR.

The gene therapy vector of the present invention can therefore be used to treat or manage monogenic forms of NS in a patient. The term "patient" as used herein may include any mammal, including a human. The patient may be an adult or a paediatric patient, such as a neonate or an infant. In embodiments of the invention the patient may be a paediatric patient between the ages of about 1 and about 16 years old.

The patient is suffering from a monogenic form of NS. In other words, the NS is caused by a mutation in one gene. Preferably mutation is in a gene expressed in podocytes, such as one or more mutations in any one of NPHS1, TRPC6, ACTN4, TRPC6, ANKFY1, ANLN, CRB2, ITGA3, KANK1, KANK4, MAGI2, MYO1E, NUP107, NUP133, NUP160, OCRL, PTPRO, SMARCAL1, SYNPO, T8C1D8B, XPO5, TNS2 or NLRP3. In embodiments of the invention the monogenic form of NS may be a monogenic form of SRNS caused by one or more mutations in any one of NPHS1, TRPC6, ACTN4 or TRPC6. For example, the NS may be SRNS caused by a mutation in NPHS1, which codes for nephrin, a type-1 transmembrane protein found at the slit diaphragm of glomerular podocytes. The slit diaphragm functions as an ultrafilter to exclude albumin and other plasma macromolecules in the formation of urine. Mutations in NPHS1 gene result in nephrotic syndrome, with the most common mutations being associated with Finnish-type congenital nephrosis, which is characterized by severe proteinuria and loss of the slit diaphragm and foot processes. The NPHS1 mutation may be a Fin-major mutation or a Fin-minor mutation (Kestila et al).

The NS-associated transgene used in the gene therapy is a gene associated with a monogenic form of NS and expressed in podocytes, and which encodes a protein of about 1600 amino acids or less, optionally about 1500 amino acids or less, or about 1450 amino acids or less. This size limitation allows the NS-associated transgene to fit into the gene therapy vector of the present invention.

The transgene is typically included in the gene therapy vector as a cDNA sequence. However, the NS-associated transgene may be any polynucleotide, such as single or double-stranded DNA or RNA, comprising a nucleic acid sequence encoding any NS-associated polynucleotide as discussed above. For instance the NS-associated polynucleotide may comprise the NPHS1 open reading frame (ORF) sequence of FIG. 4A or 4B. The NPHS1 polynucleotide may comprise a nucleic acid sequence which has at least 85%, 90%, 95%, 96%, 97%, 98%, 99% or more sequence identity to the NPHS1 ORF sequence of FIG. 4A or 4B, as long as it encodes a nephrin polypeptide that has retained its biological activity, particularly its ability to maintain slit diaphragm integrity and/or slit diaphragm-mediated signalling. Nephrin protein consists of a C-terminal cytoplasmic domain, a transmembrane domain, a fibronectin type III-like module, eight extracellular Ig-like domains and a signal peptide domain. Preferably some or all of these structural components are conserved.

In the description above, the term "identity" is used to refer to the similarity of two sequences. For the purpose of this invention, it is defined here that in order to determine the percent identity of two sequences, the sequences are aligned for optimal comparison purposes (e.g., gaps can be introduced in the sequence of a first sequence for optimal alignment with a second amino or nucleic acid sequence). The nucleotide/amino acid residues at each position are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Generally, the two sequences are the same length. A sequence comparison is typically carried out over the entire length of the two sequences being compared.

The skilled person will be aware of the fact that several different computer programs are available to determine the identity between two sequences. For instance, a comparison of sequences and determination of percent identity between two sequences can be accomplished using a mathematical algorithm. For example, the percent identity between two nucleic acid sequences can be determined using the sequence alignment software Clone Manager 9 (Sci-Ed software—www.scied.com) using global DNA alignment; parameters: both strands; scoring matrix: linear (mismatch 2, OpenGap 4, ExtGap 1).

Alternatively, the percent identity between two amino acid or nucleic acid sequences can be determined using the Needleman and Wunsch (1970) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. A further method to assess the percent identity between two amino or nucleic acid sequences can be to use the BLAST sequence comparison tool available on the National Center for Biotechnology Information (NCBI) website (www.blast.ncbi.nlm.nih.gov), for example using BLASTn for nucleotide sequences or BLASTp for amino acid sequences using the default parameters.

The presence or absence of a monogenic form of NS can be determined by laboratory testing, such as that available from Bristol Genetics Laboratories, Bristol, UK. Typically, genetic testing can be performed by analysis of a blood sample obtained from the patient.

The AAV vector gene therapy may be administered systemically, such as by intravenous injection. In embodiments of the invention the AAV vector gene therapy may be administered by injection into the renal artery. In alternative embodiments of the invention the AAV vector gene therapy may be administered by retrograde administration, e.g. via the ureters using a urinary catheter.

The gene therapy may be administered as a single dose, in other words, subsequent doses of the vector may not be needed. In the event that repeated doses are needed different AAV serotypes can be used in the vector. For example, vector used in a first dose may comprise AAV-LK03 or AAV-3B whereas the vector used in a subsequent dose may comprise AAV 2/9.

Optionally the gene therapy may be administered in combination with temporary immunosuppression of the patient, e.g. by administering the gene therapy at the same time as, or following treatment with, oral steroids. Immunosuppression may be desirable before and/or during gene therapy treatment to suppress the patient's immune response to the vector. However, the AAV capsid is present only transiently in the transduced cell as it is not encoded by the vector. The capsid is therefore gradually degraded and cleared, meaning that a short-term immunomodulatory regimen that blocks the immune response to the capsid until capsid sequences are cleared from the transduced cells can allow long-term expression of the transgene. Immunosuppression may therefore be desirable for a period of about six weeks following administration of the gene therapy.

The AAV vector gene therapy may be administered in the form of a pharmaceutical composition. In other words the AAV vector gene therapy may be combined with one or more pharmaceutically acceptable carriers or excipients. A suitable pharmaceutical composition is preferably sterile.

BRIEF DESCRIPTION OF THE DRAWINGS

The invention will now be described in detail, by way of example only, with reference to the figures.

FIG. 1 shows an example DNA sequence for the minimal human nephrin promoter (NPHS1).

FIG. 2 shows an example DNA sequence for a WPRE sequence.

FIG. 3 shows an example DNA sequence for a bGH poly(A) signal sequence.

FIGS. 4A and B show example cDNA sequences for human NPHS1 transgenes.

EXAMPLES

A suitable AAV serotype will be used to transfect mouse and human podocytes in vitro, and mouse NS knockout models in vivo. The AAV plasmid will have a NPHS1 minimal promoter cassette, WPRE and bGH cassettes, and an SRNS cDNA sequence (i.e., a NS-associated transgene) cloned in.

REFERENCES

M. KESTILÄ, U. LENKKERI, M. MÄNNIKKÖ, J. LAMERDIN, P. MCCREADY, H. PUTAALA, V. RUOTSALAINEN, T. MORITA, M. NISSINEN, R. HERVA, C. E. KASHTAN, L. PELTONEN, C. HOLMBERG, A. OLSEN, K. TRYGGVASON. 1998. Positionally cloned gene for a novel glomerular protein—nephrin—is mutated in congenital nephrotic syndrome. Mol Cell, 1 pp. 575-582

LUO, X., HALL, G., LI, S., BIRD, A., LAVIN, P. J., WINN, M. P., KEMPER, A. R., BROWN, T. T. & KOEBERL, D. D. 2011. Hepatorenal correction in murine glycogen storage disease type I with a double-stranded adeno-associated virus vector. Mol Ther, 19, 1961-70.

MOELLER, M. J., SANDEN, S. K., SOOFI, A., WIGGINS, R. C. & HOLZMAN, L. B. 2002. Two gene fragments that direct podocyte-specific expression in transgenic mice. J Am Soc Nephrol, 13, 1561-7.

PICCONI, J. L., MUFF-LUETT, M. A., WU, D., BUNCHMAN, E., SCHAEFER, F. & BROPHY, P. D. 2014.

Kidney-specific expression of GFP by in-utero delivery of pseudotyped adeno-associated virus 9. Molecular Therapy Methods & Clinical Development, 1, 14014.

ROCCA, C. J., UR, S. N., HARRISON, F. & CHERQUI, S. 2014. rAAV9 combined with renal vein injection is optimal for kidney-targeted gene delivery: conclusion of a comparative study. Gene therapy, 21, 618-628.

SCHAMBACH, A., BONNE, J., BAUM, C., HERMANN, F. G., EGERER, L., VON LAER, D. & GIROGLOU, T. 2005. Woodchuck hepatitis virus post-transcriptional regulatory element deleted from X protein and promoter sequences enhances retroviral vector titer and expression. Gene Therapy, 13, 641.

SCHIEVENBUSCH, S., STRACK, I., SCHEFFLER, M., NISCHT, R., COUTELLE, O., HOSEL, M., HALLEK, M., FRIES, J. W. U., DIENES, H.-P., ODENTHAL, M. & BONING, H. 2010. Combined Paracrine and Endocrine AAV9 mediated Expression of Hepatocyte Growth Factor for the Treatment of Renal Fibrosis. Molecular Therapy, 18, 1302-1309.

VAN DER WOUDEN, E. A., SANDOVICI, M., HENNING, R. H., DE ZEEUW, D. & DEELMAN, L. E. 2004. Approaches and methods in gene therapy for kidney disease. J Pharmacol Toxicol Methods, 50, 13-24.

The invention claimed is:

1. An adeno-associated virus (AAV) vector comprising:
a nephrotic syndrome-associated transgene; and
a minimal nephrin promoter or a minimal podocin promoter,
wherein the nephrotic syndrome-associated transgene is selected from one or more of NPHS1, TRPC6, NUP107, NUP133, NUP160, ACTN4, INF2, ANKFY1, ANLN, CRB2, ITGA3, KANK1, KANK4, MAGI2, MYO1E, OCRL, PTPRO, SMARCAL1, SYNPO, TBC1D8B, XPO5, TNS2 or NLRP3, and
wherein the AAV vector is AAV serotype LK03 or 3B.

2. The AAV vector according to claim 1, wherein the AAV vector additionally comprises a Woodchuck hepatitis post-transcriptional regulatory element (WPRE).

3. The AAV vector according to claim 1, wherein the nephrotic syndrome-associated transgene is human.

4. The AAV vector according to claim 1, wherein the AAV vector additionally comprises a Kozak sequence between the promoter and the nephrotic syndrome-associated transgene.

5. The AAV vector according to claim 1, wherein the AAV vector additionally comprises a polyadenylation signal.

6. A method of treating a monogenic form of nephrotic syndrome comprising administering an AAV vector according to claim 1 to a patient with the monogenic form of nephrotic syndrome.

7. The method according to claim 6, wherein the monogenic form of nephrotic syndrome is a monogenic form of steroid-resistant nephrotic syndrome.

8. The method according to claim 6, wherein the patient is human.

9. The method according to claim 8, wherein the patient is a paediatric patient.

10. The method according to claim 6, wherein the AAV vector is administered systemically.

11. The method according to claim 6, wherein the AAV vector is administered by intravenous injection.

12. The method according to claim 6, wherein the AAV vector is administered by injection into the renal artery.

13. The AAV vector according to claim 5, wherein the polyadenylation signal is a bovine growth hormone (bGH) polyadenylation signal.

14. The AAV vector according to claim 1, wherein the AAV vector is AAV serotype LK03.

15. The AAV vector according to claim 1, wherein the AAV vector is AAV serotype 3B.

16. The method according to claim 8, wherein the patient is an adult.

* * * * *